US005703040A

United States Patent [19]

Iandolo et al.

[11] Patent Number: 5,703,040
[45] Date of Patent: Dec. 30, 1997

[54] BROAD SPECTRUM ANTIBIOTIC PEPTIDE

[75] Inventors: John J. Iandolo; Scott Crupper, both of Manhattan, Kans.

[73] Assignee: Kansas State University Research Foundation, Manhattan, Kans.

[21] Appl. No.: 561,935

[22] Filed: Nov. 22, 1995

[51] Int. Cl.$^6$ .................... A01N 37/18; C09F 00/00; C07K 1/00; A61K 38/00
[52] U.S. Cl. .................. 514/2; 530/200; 530/350; 530/825
[58] Field of Search .................. 514/2; 530/300, 530/200, 825, 350

[56] References Cited

U.S. PATENT DOCUMENTS 4,980,163 12/1990 Blackburn et al. ................. 434/94.63

OTHER PUBLICATIONS

Bhunia, A. K., M. C. Johnson and B. Ray. J. Indust. Microbiol. 2:319 (1987).
Dajani, A.S., E. D. Gray and L.W. Wannamaker, J.Exp. Med. 131:1004 (1970).
Lewus, C. B., A. Kaiser and T. J. Montville, Appl. Environ. Microbiol. 57:1683 (1991).
Miles, H., W. Lesser and P. Sears, J. Dairy Sci. 75:596 (1992).
Hurst, A. Adv. Appl. Microbiol. 27:85 (1981).
Jung, G. Agnew. Chem. In the Ed. Engl. 30:1051 (1991).
Tagg, J.R., A. S. Dajani and L. W. Wannamaker. Bacteriol. Rev. 40:722 (1976).
Jackson, M. P. and J. Iandolo, J. Bacteriol. 166:574-580 (1986).
Masterson, R., W. V. David, B. B. Wiley, M. Rogolsky. Infection and Immunity. 42:973-79 (1983).
Rogolsky et al.; Production and Properties of a Staphylococcin Genetically Controlled by the Staphylococccal Plasmid for Exfoliative Toxin Synthesis; Infection and Immunity 15:726-732 (1977).
Sears et al.; Evaluation of a Nisin-Based Germicidal Formulation on Teat Skin of Live Cows; J. Dairy Sci. (75) 3185-3190 (1992).

*Primary Examiner*—Douglas W. Robinson
*Assistant Examiner*—Kent L. Bell
*Attorney, Agent, or Firm*—Hovey, Williams, Timmons & Collins

[57] ABSTRACT

Improved antimicrobial proteinaceous substances produced by *Staphylococcus aureus* KSI1829 (e.g., Bac1829) and methods of inhibiting microbial growth using such substances are disclosed.

31 Claims, 4 Drawing Sheets

BROAD SPECTRUM ANTIBIOTIC PEPTIDE

This invention was made with government support under Grant AI-17474 awarded by the Department of Health and Human Services/National Institutes of Health. The government has certain rights in the invention.

BACKGROUND OF THE INVENTION

1. Field of the Invention

The present invention is broadly concerned with improved antimicrobial proteinaceous substances produced by Staphylococcus and with methods of inhibiting microbial growth using these substances. More particularly, the invention in its preferred form is directed to Bac1829, a novel 6.4-kilodalton antimicrobial peptide produced by *Staphylococcus aureus* KSI1829.

2. Description of the Prior Art

Many bacteria produce bacteriocins, agents that inhibit or kill closely related species. Bacteriocins are a diverse group of substances. They are usually protein, and are frequently of high molecular weight. Additionally, bacteriocin-like inhibitory substances (BLIS) have been isolated from the following genera: the spore formers Bacillus and Clostridium; the lactic acid bacteria Lactobacillus, Streptococcus, Pediococcus, and Leuconostoc; and the micrococci including various strains of Staphylococcus (1). BLIS are often named according to their origin. For example, staphylococcins and aureocins are produced by *Staphylococcus aureus*.

BLIS are a heterogenous group of substances whose single unifying property is that they are proteins. They range from small peptides (e.g., the antibiotics nisin of *Enterococcus lactis* and epidermin of *Staphylococcus epidermidis* (2)) to large proteins complexed with lipids and carbohydrates (e.g., staphylococcin 414 (3)). BLIS of low molecular weight often contain rare amino acids such as lanthionine, are relatively heat resistant, are sensitive to proteolytic enzymes, and exhibit great hydrophobicity, tending to form aggregates in solution (1). This last property has made the purification of BLIS difficult. However, aggregation is diminished by the presence of 6M urea, detergents, high ionic strength, and low pH. The antigenicity of BLIS is a controversial subject. BLIS of high molecular weight have elicited neutralizing antibodies. However, BLIS of low molecular weight from Staphylococcus have not been shown to be antigenic.

Disease control using bacteriocin is cheap, effective, and non-toxic to non-target organisms including animals and humans (4, 5). For example, nisin used topically is as effective as a 1% iodophor dip in controlling both gram-positive and gram-negative bacteria inoculated onto teat skin of live cows (6). Furthermore, treatment with nisin does not irritate skin, even after multiple applications. In addition, since bacteriocins are GRAS compounds (i.e., generally recognized as safe by the Food and Drug Administration), milk from bacteriocin-treated cows is not considered adulterated. Therefore, the milk can be brought to market without a holding period.

SUMMARY OF THE INVENTION

The present invention concerns at least partially purified antimicrobial proteinaceous substances produced by Staphylococcus having a molecular weight of from about 6 to 7 kilodaltons. In preferred embodiments, the substance is purified from cell cultures, is essentially protein, and has a molecular weight of about 6.4 kilodaltons. Furthermore, the substance at a concentration of 640 antimicrobial units/ml in an aqueous solution retains essentially all of its antimicrobial activity after one or more of the following treatments: (1) heat treatment at 95° C. for 15 minutes, (2) treatment with 6M urea or 10 mM dithiothreitol at room temperature for 1 hour, and (3) treatment with deoxyribonuclease, ribonuclease, or lysostaphin at a concentration of 1 mg/ml at room temperature for 1 hour. Additionally, the substance at a concentration of 640 antimicrobial units/ml in an aqueous solution loses essentially all of its antimicrobial activity after being treated at room temperature for 1 hour with proteinase K or trypsin at a concentration of 1 mg/ml. Moreover, the substance at a concentration of 1280 antimicrobial units/ml has antimicrobial activity against one or more of the following organisms: *Staphyloccocus aureus* 8325-4r, *Streptococcus suis*, *Corynebacterium renale*, *Corynebacterium pseudotuberculosis* Whetten 1, *Corynebacterium diptheriae*, *Haemophilus parasuis*, *Bordetella pertussis*, *Bordetella brochoseptica*, *Moraxella bovis*, and *Pasteurella multocida*. Preferably, the substance is Bac1829, a 6.4-kilodalton protein produced by *Staphylococcus aureus* KSI1829. *Staphylococcus aureus* KSI1829 has been deposited in the American Type Culture Collection, Rockville, Md. under the terms of the Budapest Treaty and has been accorded Accession No. 55716. The invention also includes methods of inhibiting microbial growth in an environment capable of sustaining such growth. This method comprises administering to this environment a microbial growth-inhibiting amount of the substance (e.g., applying the substance topically on the teat skin of cows to control bacterial growth, and using the substance as an antibiotic to prevent or eradicate bacterial infection in an animal).

DETAILED DESCRIPTION OF THE PREFERRED EMBODIMENTS

Figure 1:
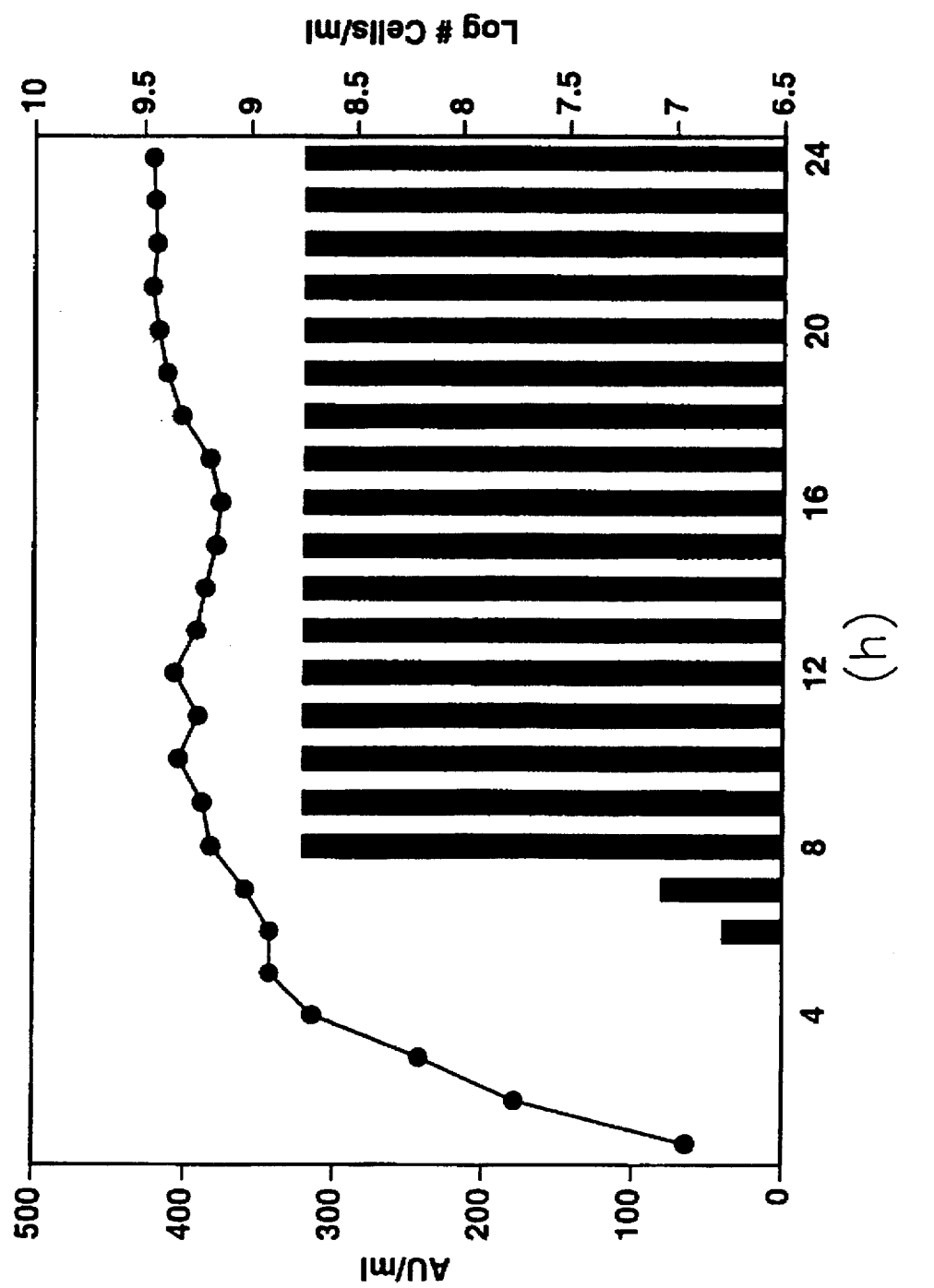
FIG. 1 is a pair of graphs illustrating the growth of *S. aureus* KSI1829 in 2X-YT media at 37° C. with shaking (line) and corresponding secretion of Bac1829 measured by bactericidal assay of culture supernatant bacteriocins (bars)

The following examples describe the purification and characterization of Bac1829, an improved antimicrobial proteinaceous substance produced by *Staphylococcus aureus* KSI1829, and its use in inhibiting microbial growth. The examples are set forth by way of illustration only, and nothing therein shall be taken as a limitation upon the overall scope of the invention.

EXAMPLE 1

Bacterial Strains and Media

*Staphylococcus aureus* KSI1829, a derivative of *S. aureus* 8325-4r, is a laboratory isolate and is propagated at 37° C. in 2X-YT medium with shaking at 180 rpm [16 g/L Bactotryptone (Difco Laboratories, Detroit, Mich.), 10 g/L Bactoyeast extract (Difco Laboratories, Detroit, Mich.), and 5 g/L NaCl]. *Corynebacterium renale* ATCC 19412 was used as the indicator strain in bactericidal assays and is routinely grown at 37° C. in brain heat infusion media (Difco) containing 0.3% Tween-80 (BHT-80).

EXAMPLE 2

Bactericidal Assay of Bac1829

Bactericidal activity of Bac1829 was determined by dilution analysis on BHT-80 agar plates containing *C. renale*. To prepare *C. renale* plates, 60 μl of an overnight culture of *C. renale* were added to 20 ml of liquified BHT-80 agar held at 45° C. The inoculated agar was poured into Petri dishes. After solidification, 3 mm wells were bored in the agar with a gel punch. Bactericidal activity was assayed by adding 20 μl of solutions containing Bac1829 to each well and incubating the plates at 37° C. overnight. Bactericidal activity was evident the next day as a zone of growth inhibition surrounding the well. This activity was measured in antimicrobial units (AU), defined as the reciprocal of the highest dilution demonstrating inhibitory activity.

EXAMPLE 3

SDS-PAGE Bioassay of Bac1829

An HPLC-purified preparation of Bac1829 was subjected to electrophoretic analysis by SDS-PAGE. The resultant Bac1829 band in the gel was bioassayed using a slight modification of the method of Bhunia et al. (7). Briefly, the protein sample was electrophoresed in a 10–20% SDS-PAGE gradient gel (Bio-Rad, Richmond, Calif.) as previously described (8). After electrophoresis, SDS was removed by soaking the gel in 20% isopropanol-10% acetic acid in water for 2 h, followed by rinsing in distilled water for 4 h. The gel was then placed on a BHT-80 agar plate and overlaid with BHT-80 top agar (BHT-80+0.7% agar) containing *C. renale*. After incubation at 37° C. overnight, the plate/gel combination was examined for zones of growth inhibition.

EXAMPLE 4

Purification of Bac1829

An overnight culture of KSI1829 was used to inoculate 2X-YT medium to an $A_{600}$ of 0.05. The cultures were incubated at 37° C. for 12–18 h with shaking at 180 rpm and the cells were removed by centrifugation at 4,000 xg for 15 min. The clarified culture supernatant was concentrated by first adding solid ammonium sulfate to 50% saturation at 4° C. with constant stirring. Previous experiments had shown that bactericidal activity is not precipitated at 50% saturation of ammonium sulfate. Therefore, the resultant surface pellicle was discarded, and additional ammonium sulfate was added to 70% saturation. After constant stirring for 20 min to dissolve the salt, the solution was centrifuged at 4° C. at 9,000 xg for 15 min. The precipitate was collected and dissolved in 1/100 of the initial culture volume in phosphate-buffered saline (PBS) containing 6M urea (pH 7.0). The solution was then chromatographed on a column of Sephadex G-50 (34×5 cm) and eluted with the same buffer. Column fractions were subjected to protein analysis by measuring the $A_{280}$, and to bactericidal assay. Fractions (10 ml) demonstrating bactericidal activity were pooled and concentrated by ammonium sulfate precipitation (70% saturation). Precipitated protein was redissolved in a minimal volume of 0.1M sodium phosphate (pH 7.0).

Final purification was achieved by high-performance liquid chromatography (HPLC) using a SynChropak propyl hydrophobic-interaction column (250×4.6 mM) equilibrated in 0.1M sodium phosphate-2M ammonium sulfate (pH 7.0) (SynChrom, Inc., Lafayette, Ind.). Protein was eluted using a reverse gradient of 2M to 0M $(NH_4)_2SO_4$ in phosphate buffer (pH 7.0). The $(NH_4)_2SO_4$ gradient was generated over a period of 45 min with a rate of 1 ml/min. The $A_{220}$ of eluent was measured and 1 ml fractions were collected. Fractions containing bactericidal activity were dialyzed in 3,500 dalton cutoff dialysis tubing (Spectrapor, Los Angeles, Calif.) overnight at 4° C. against distilled water. The samples were then taken to dryness in a speedvac and resuspended in PBS (pH 7.4). Total protein was estimated by measuring the $A_{280}$ of the solution.

EXAMPLE 5

Determination of Stability of Bac1829

The stability of Bac1829 was assessed by determining the activity of Bac1829 by bactericidal assay after exposure to various temperatures, environmental conditions, and enzymes (Table 2). Solutions of HPLC-purified Bac1829 at a concentration of 640 AU/ml were used in these stability experiments. Bac1829 samples were held at various temperatures for 15 min, were incubated in 6M urea or in 10 mM dithiotreitol (DTT) at room temperature for 1 h, or were incubated with 1 mg/ml of enzyme at room temperature for 1 h.

EXAMPLE 6

Amino Acid Analysis of Bac1829

Amino acid analysis was carried out at the Kansas State University Biotechnology facilities on an Applied Biosystems Model 420A Amino Acid analysis system (Applied Biosystems, Foster City, Calif.).

EXAMPLE 7

Determination of Inhibitory Spectrum of Bac1829

Bactericidal activity of Bac1829 against various test organisms (Table 4) was determined using the bactericidal assay, except that *C. renale* was replaced by each test organism. Sephadex G-50 column-purified Bac1829 at a concentration of 1280 AU/ml was added to each plate. Control experiments were conducted using protein preparations from *S. aureus* 8325-4r at the same level of purification as Bac1829.

RESULTS

Production of Bac1829

Cultures of *S. aureus* KSI1829 were found to contain maximal amounts of Bac1829 at 8 h after inoculation which corresponded with the onset of stationary phase growth (FIG. 1). The peptide is quite stable in culture as evidenced by the fact that the amount of Bac1829 did not decrease even after incubation of cultures for 24 h. Therefore, for convenience, all cultures of KSI1829 were harvested at 12–18 h.

Purification of Bac 1829

Figure 2:
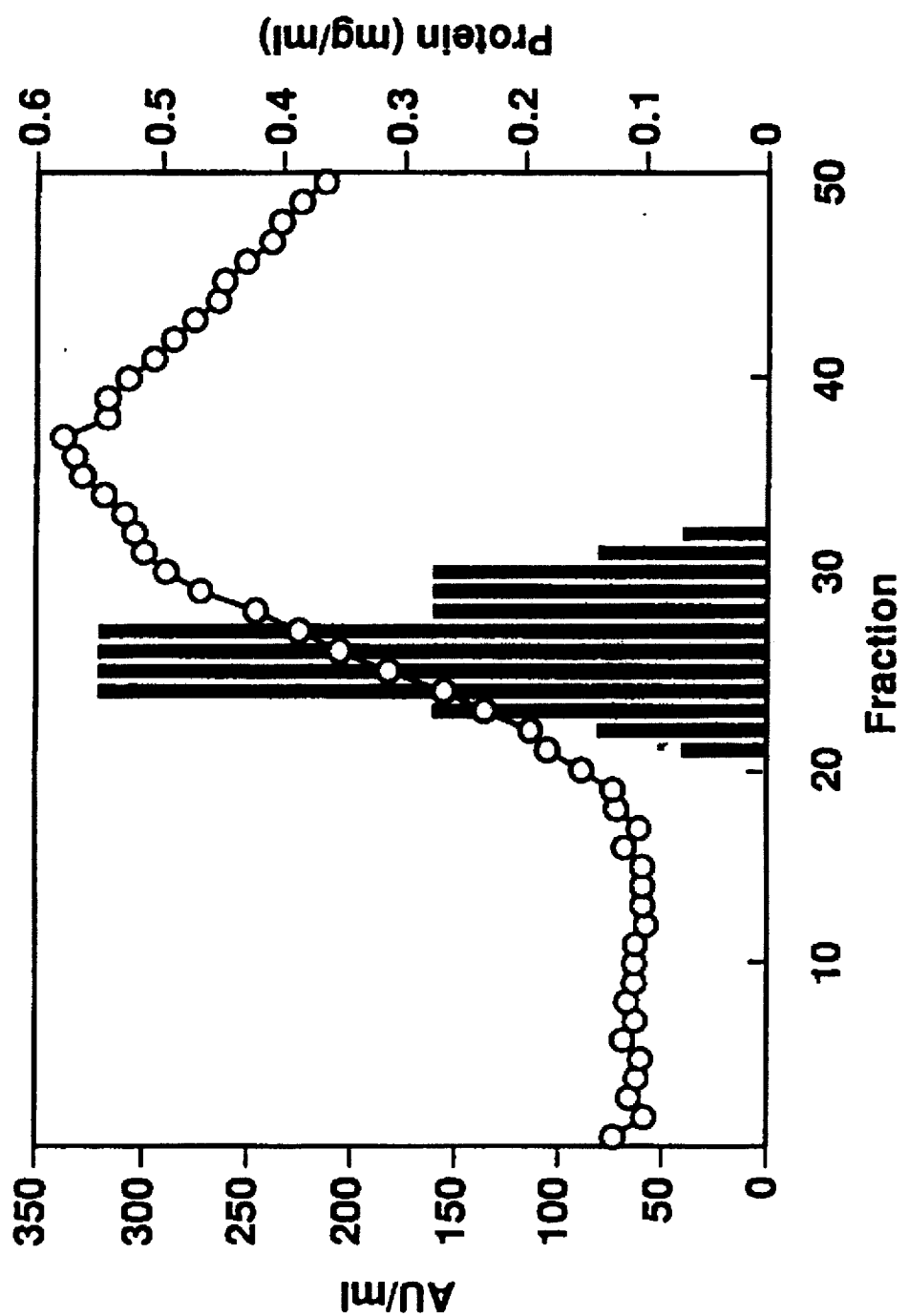
FIG. 2 is a pair of graphs illustrating the elution profile of Bac1829 from a Sephadex G-50 gel-filtration column, with the line representing the protein concentration of fractions and the bars representing bactericidal activity of fractions.

The results of the purification of Bac1829 are summarized in Table 1. The addition of ammonium sulfate to a final concentration of 70% resulted in precipitation of 96% of the total Bac1829 activity. Bactericidal activity obtained after ammonium sulfate precipitation was fractionated by Sephadex G-50 chromatography (FIG. 2). Bac1829 activity eluted over several fractions which were pooled and concentrated by ammonium sulfate precipitation (75% saturation). This step resulted in a moderate (1.5-fold) increase in specific activity.

Figure 3:
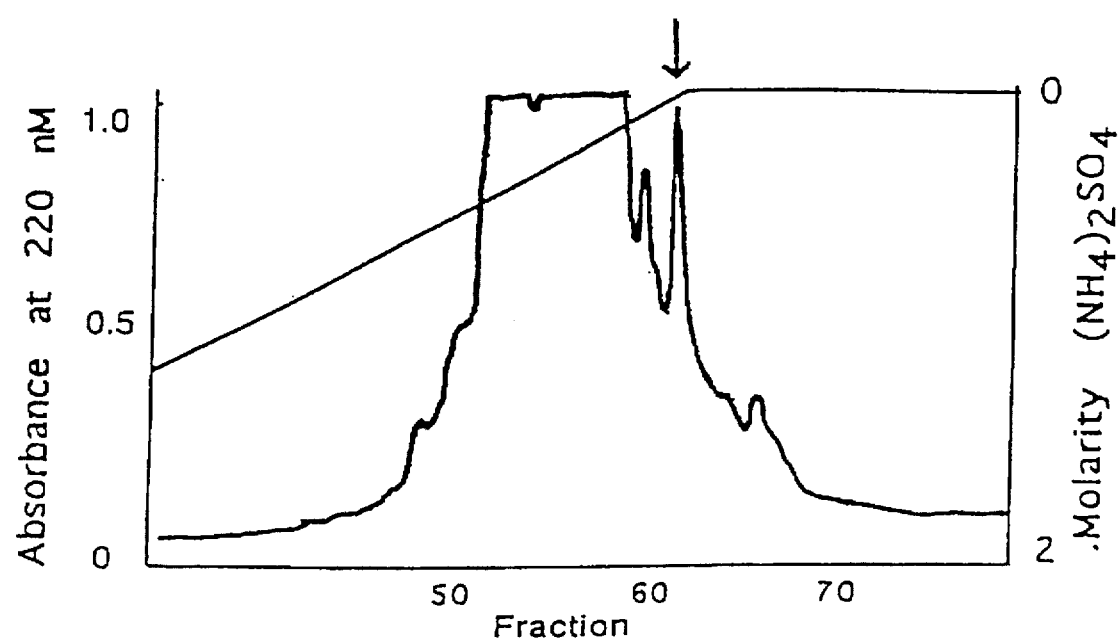
FIG. 3 is a pair of graphs illustrating the elution profile of Sephadex G-50-purified Bac1829 activity after high-performance liquid chromatography (HPLC) using a reverse gradient of ammonium sulfate, with the arrow denoting the Bac1829 peak.
Figure 4:
FIGS. 4 (A and B) are photographs of a silver-stained SDS-PAGE gel of HPLC-purified Bac1829 (FIG. 4A) and an SDS-PAGE gel of HPLC-purified Bac1829 overlaid with BHTA top agar seeded with *C. renale* (FIG. 4B).

Bac1829 activity recovered by gel filtration was further purified by HPLC, i.e., hydrophobic-interaction chromatography using a propyl column (FIG. 3). A single peak contained the bactericidal activity. Fractions corresponding to this peak were dialyzed overnight against $dH_2O$ and taken to dryness by evaporation. Analysis of the dried fractions by SDS-PAGE revealed a single silver-staining protein band that also possessed bactericidal activity against *C. renale* (FIG. 4). This preparation of Bac1829 demonstrated a 114-fold increase in specific activity.

TABLE 1

Purification of Bac1829.

| Purification Stage | Total Protein (mg/ml) | Total Activity (AU)[a] | Specific Activity (Au/mg)[b] | Yield % | Fold Purification |
|---|---|---|---|---|---|
| Supernatant (0.5 L) | 197.5 | 36,000 | 182 | 100 | 1 |
| Ammonium sulfate ppt. | 130.3 | 34,544 | 265 | 96 | 1.5 |
| Sephadex G-50 | 7.4 | 10,160 | 1,377 | 28 | 7.5 |
| Hydrophobic interaction | 0.21 | 4,352 | 20,724 | 0.12 | 114 |

[a]Determined by bactericidal assay.
[b]Specific activity is AU divided by the total protein.

Physical and Chemical Properties of Bac 1829

HPLC-purified Bac1829 was tested for sensitivity to heat and various environmental and enzymatic conditions (Table 2). Bac1829 can be classified as heat-stable since full bactericidal activity was retained after heating at 95° C. for 15 min. Additionally, Bac1829 was not inactivated by treatment with 6M urea, 10 mM DTT, deoxyribonuclease (DNase), ribonuclease (RNase), or lysostaphin; however, proteinase K and trypsin destroyed bactericidal activity.

TABLE 2

Physical properties of Bac1829.

| Treatment[a] | % Residual Activity |
|---|---|
| −20° C. | 100 |
| 4° C. | 100 |
| 25° C. | 100 |
| 37° C. | 100 |
| 95° C. | 100 |
| 6 M urea | 100 |
| 10 mM DTT | 100 |
| DNase | 100 |
| RNase | 100 |
| lysostaphin | 100 |
| proteinase K | 0 |
| trypsin | 0 |

[a]Bac1829 samples were held at the indicated temperatures for 15 min, and at room temperature for 1 h for all other treatments.

Chemical Composition of Bac1829

Analysis of an HPLC-purified preparation of Bac1829 by mass spectrometry showed that the peptide has a molecular weight of 6418 daltons. Amino acid analysis (Table 3) revealed an inordinately high concentration of glycine, threonine and alanine residues. As expected, high levels of hydrophobic amino acids were present, accounting for the hydrophobic nature of Bac1829.

TABLE 3

Amino acid composition of Bac1829.

| Amino Acid | Molar % |
|---|---|
| Asx | 1.50 |
| Glx | 6.09 |
| Ser | 8.71 |
| Gly | 12.80 |
| His | 0.97 |
| Arg | 0.28 |
| Thr | 11.76 |
| Ala | 19.50 |
| Pro | 2.32 |
| Tyr | 1.95 |
| Val | 6.65 |
| Met | 1.29 |
| Ile | 4.25 |
| Leu | 8.96 |
| Phe | 3.32 |
| Lys | 9.92 |
| Cys | 0.36 |
| Trp | Not Determined |

Inhibitory Spectrum of Bac1829

Bactericidal assays were performed using various test organisms to determine the inhibitory spectrum of Bac1829. Sephadex G-50 column-purified Bac1829 inhibited the growth of several different genera of bacteria as demonstrated by zones of growth inhibition on indicator plates (Table 4). Protein preparations from *S. aureus* 8325-4r (the parent of KSI1829) at the same level of purification as Bac1829 did not inhibit growth of the test organisms (data not shown), demonstrating that Bac1829 is produced by KSI1829 but not by its parent.

TABLE 4

Inhibitory spectrum of Sephadex G-50 column-purified Bac1829.

| Test Organism | Susceptibility[a] |
|---|---|
| *Escherichia coli* | − |
| *Enterococcus faecalis* JH2-2 | − |
| *Salmonella typhimurium* | − |
| *Haemophilus somnus* | − |
| *Actinobacillus pleuropneumoniae* | − |
| *Staphyloccocus aureus* 8325-4r⁻ | + |
| *Streptococcus suis* | + |
| *Corynebacterium renale* | + |
| *Corynebacterium pseudotuberculosis* Whetten 1 | + |
| *Corynebacterium diptheriae* | + |
| *Haemophilus parasuis* | + |
| *Bordetella pertussis* | + |
| *Bordetella brochoseptica* | + |
| *Moraxella bovis* | + |
| *Pasteurella multocida* | + |

[a]Susceptibility (+) of test organisms to Bac1829 was demonstrated by bactericidal assays in which zones of growth inhibition surrounded wells in indicator plates, while resistance (−) was demonstrated by the lack of zones of growth inhibition.

REFERENCES

The teachings of the following references are herein incorporated by reference:

1. Tagg, J. R., A. S. Dajani and L. W. Wannamaker. Bacteriol. Rev. 40:722 (1976).
2. Jung, G. Angew. Chem. Int. Ed. Engl. 30:1051 (1991).
3. Hurst, A. Adv. Appl. Microbiol. 27:85 (1981).

4. Miles, H., W. Lesser and P. Sears. J. Dairy Sci. 75:596 (1992).
5. Lewus, C. B., A. Kaiser and T. J. Montville. Appl. Environ. Microbiol. 57:1683 (1991).
6. Sears, P. M., B. S. Smith, W. K. Stewart, R. N. Gonzalez, S. D. Rubino, S. A. Gusik, E. S. Kulisek, S. J. Projan and P. Blackburn. J. Dairy Sci. 75:3185 (1992).
7. Laemmli, U .K. Nature(London). 227:680 (1970).
8. Bhunia, A. K., M. C. Johnson, and B. Ray. J. Indust. Microbiol. 2:319 (1987).

We claim:

1. An at least partially purified antimicrobial proteinaceous substance produced by Staphyloccocus aureus having a molecular weight of from about 6 to 7 kilodaltons, wherein said substance at a concentration of 640 antimicrobial units/ml in an aqueous solution retains essentially all of its antimicrobial activity after one or more of the following treatments: (1) heat treatment at 95° C. for 15 minutes, (2) treatment with 6M urea or 10 mM dithiothreitol at room temperature for 1 hour, and (3) treatment with deoxyribonuclease, ribonuclease, or lysostaphin at a concentration of 1 mg/ml at room temperature for 1 hour.

2. The substance of claim 1, wherein said Staphylococcus is Staphylococcus aureus KSI1829.

3. The substance of claim 1, wherein said Staphylococcus is grown in a cell culture.

4. The substance of claim 1, wherein said molecular weight is about 6.4 kilodaltons.

5. The substance of claim 1, wherein said substance is a protein.

6. The substance of claim 1, wherein said substance is Bac1829.

7. The substance of claim 1, wherein said substance at a concentration of 640 AU/ml in an aqueous solution retains its antimicrobial activity after being heated at 95° C. for 15 minutes.

8. The substance of claim 1, wherein said substance at a concentration of 640 AU/ml in an aqueous solution retains its antimicrobial activity after being treated at room temperature for 1 hour with urea at a concentration of 6M.

9. The substance of claim 1, wherein said substance at a concentration of 640 AU/ml in an aqueous solution retains its antimicrobial activity after being treated at room temperature for 1 hour with dithiothreitol at a concentration of 10 mM.

10. The substance of claim 1, wherein said substance at a concentration of 640 AU/ml in an aqueous solution retains its antimicrobial activity after being treated at room temperature for 1 hour with an enzyme at a concentration of 1 mg/ml, said enzyme being selected from the group consisting of deoxyribonuclease, ribonuclease, and lysostaphin.

11. The substance of claim 1, wherein said substance at a concentration of 640 AU/ml in an aqueous solution loses its antimicrobial activity after being treated at room temperature for 1 hour with an enzyme at a concentration of 1 mg/ml, said enzyme being selected from the group consisting of proteinase K and trypsin.

12. The substance of claim 9, wherein said substance at a concentration of at least 1280 AU/ml has antimicrobial activity against a microorganism selected from the group consisting of Staphyloccocus aureus 8325-4r, Streptococcus suis, Corynebacterium renale, Corynebacterium pseudotuberculosis Whetten 1, Corynebacterium diptheriae, Haemophilus parasuis, Bordetella pertussis, Bordetella brochoseptica, Moraxella bovis, and Pasteurella multocida.

13. The substance of claim 12, wherein said antimicrobial activity inhibits the growth of said microorganism.

14. The substance of claim 13, wherein said antimicrobial activity prevents the growth of said microorganism.

15. A method of inhibiting microbial growth in an environment capable of sustaining said growth comprising administering to said environment a microbial growth-inhibiting amount of an at least partially purified antimicrobial proteinaceous substance produced by Staphylococcus aureus having a molecular weight of from about 6 to 7 kilodaltons, wherein said substance at a concentration of 640 antimicrobial units/ml in an aqueous solution retains essentially all of its antimicrobial activity after one or more of the following treatment: (1) heat treatment at 95° C. for 15 minutes, (2) treatment with 6M urea or 10 mM dithiothreitol at room temperature for 1 hour, and (3) treatment with deoxyribonuclease, ribonuclease, or lysostaphin at a concentration of 1 mg/ml at room temperature for 1 hour.

16. The method of claim 15, wherein said method prevents said microbial growth.

17. The method of claim 15, wherein said Staphylococcus is Staphylococcus aureus KSI1829.

18. The method of claim 15, wherein said Staphylococcus is grown in a cell culture.

19. The method of claim 15, wherein said molecular weight is about 6.4 kilodaltons.

20. The method of claim 15, wherein said substance is a protein.

21. The method of claim 15, wherein said substance is Bac1829.

22. The method of claim 15, wherein said substance at a concentration of 640 AU/ml in an aqueous solution retains its antimicrobial activity after being heated at 95° C. for up to 15 minutes.

23. The method of claim 15, wherein said substance at a concentration of 640 AU/ml in an aqueous solution retains its antimicrobial activity after being treated at room temperature for 1 hour with urea at a concentration of 6M.

24. The method of claim 15, wherein said substance at a concentration of 640 AU/ml in an aqueous solution retains its antimicrobial activity after being treated at room temperature for 1 hour with dithiothreitol at a concentration of 10 mM.

25. The method of claim 15, wherein said substance at a concentration of 640 AU/ml in an aqueous solution retains its antimicrobial activity after being treated at room temperature for 1 hour with an enzyme at a concentration of 1 mg/ml, said enzyme being selected from the group consisting of deoxyribonuclease, ribonuclease, and lysostaphin.

26. The method of claim 15, wherein said substance at a concentration of 640 AU/ml in an aqueous solution loses its antimicrobial activity after being treated at room temperature for 1 hour with an enzyme at a concentration of 1 mg/ml, said enzyme being selected from the group consisting of proteinase K and trypsin.

27. The method of claim 1, wherein said substance at a concentration of at least 1280 AU/ml has antimicrobial activity against a microorganism selected from the group consisting of Staphyloccocus aureus 8325-4r, Streptococcus suis, Corynebacterium renale, Corynebacterium pseudotuberculosis Whetten 1, Corynebacterium diptheriae, Haemophilus parasuis, Bordetella pertussis, Bordetella brochoseptica, Moraxella bovis, and Pasteurella multocida.

28. The method of claim 27, wherein said antimicrobial activity inhibits the growth of said microorganism.

29. The method of claim 28, wherein said antimicrobial activity prevents the growth of said microorganism.

30. The substance of claim 1, said substance being a purified peptide.

31. The method of claim 15, said substance being a purified peptide.

* * * * *